United States Patent [19]

Lucero et al.

[11] 4,036,915
[45] July 19, 1977

[54] TEMPERATURE-CONTROLLED APPARATUS FOR FLUID PERMEATION OR THE LIKE

[75] Inventors: Daniel P. Lucero, Triangle; Alan R. Teets, Springfield, both of Va.

[73] Assignee: Meloy Laboratories, Inc., Springfield, Va.

[21] Appl. No.: 430,572

[22] Filed: Jan. 3, 1974

Related U.S. Application Data

[62] Division of Ser. No. 320,624, Jan. 2, 1973, Pat. No. 3,904,849.

[51] Int. Cl.[2] .............................................. B01F 3/04
[52] U.S. Cl. .................................... 261/104; 73/1 R; 219/343; 261/130; 261/142; 261/154
[58] Field of Search ................ 261/95, 99, 103, 104, 261/107, 129, 131, 142, 122, 152–156, DIG. 54, 130; 73/1 R; 219/343; 137/3, 93; 48/DIG. 5

[56] References Cited

U.S. PATENT DOCUMENTS

| | | | |
|---|---|---|---|
| 1,798,065 | 3/1931 | Clark | 261/156 |
| 2,358,285 | 9/1944 | Johnson | 261/99 X |
| 2,430,841 | 11/1947 | Wulfhorst | 261/99 X |
| 2,612,357 | 9/1952 | Parks | 261/154 |
| 2,939,311 | 6/1960 | Booth | 261/104 X |
| 3,316,166 | 4/1967 | Bergson et al. | 261/122 X |
| 3,435,592 | 4/1969 | Lindenmaier et al. | 261/142 X |
| 3,516,278 | 6/1970 | Klein et al. | 73/1 R |
| 3,520,194 | 7/1970 | Adams | 73/1 R |
| 3,618,911 | 11/1971 | Martin | 261/104 |
| 3,758,081 | 9/1973 | Prudhon | 261/DIG. 54 |
| 3,824,836 | 7/1974 | Lyshkow | 73/1 R |
| 3,833,016 | 9/1974 | Lucero et al. | 261/104 X |

*Primary Examiner*—Tim R. Miles
*Assistant Examiner*—Richard L. Chiesa
*Attorney, Agent, or Firm*—Shapiro and Shapiro

[57] ABSTRACT

Precisely controlled permeation of a fluid into a carrier gas is provided in a temperature-controlled enclosure. A cylindrical housing has its side wall spaced from the side wall of a hollow cylindrical core contained therein to provide a thin flow passage therebetween for the carrier fluid. An electric heater coil is wound about the exterior of the housing to supply heat to the carrier fluid in the passage, and the core has a port at one end thereof for providing communication between the passage and the hollow interior of the core, in which a permeation tube is supported. The heater power output is controlled in response to a temperature sensor within the core so that the carrier fluid is heated and its temperature is precisely controlled. The exterior of the housing is insulated from ambient to maintain stable temperature conditions.

7 Claims, 7 Drawing Figures

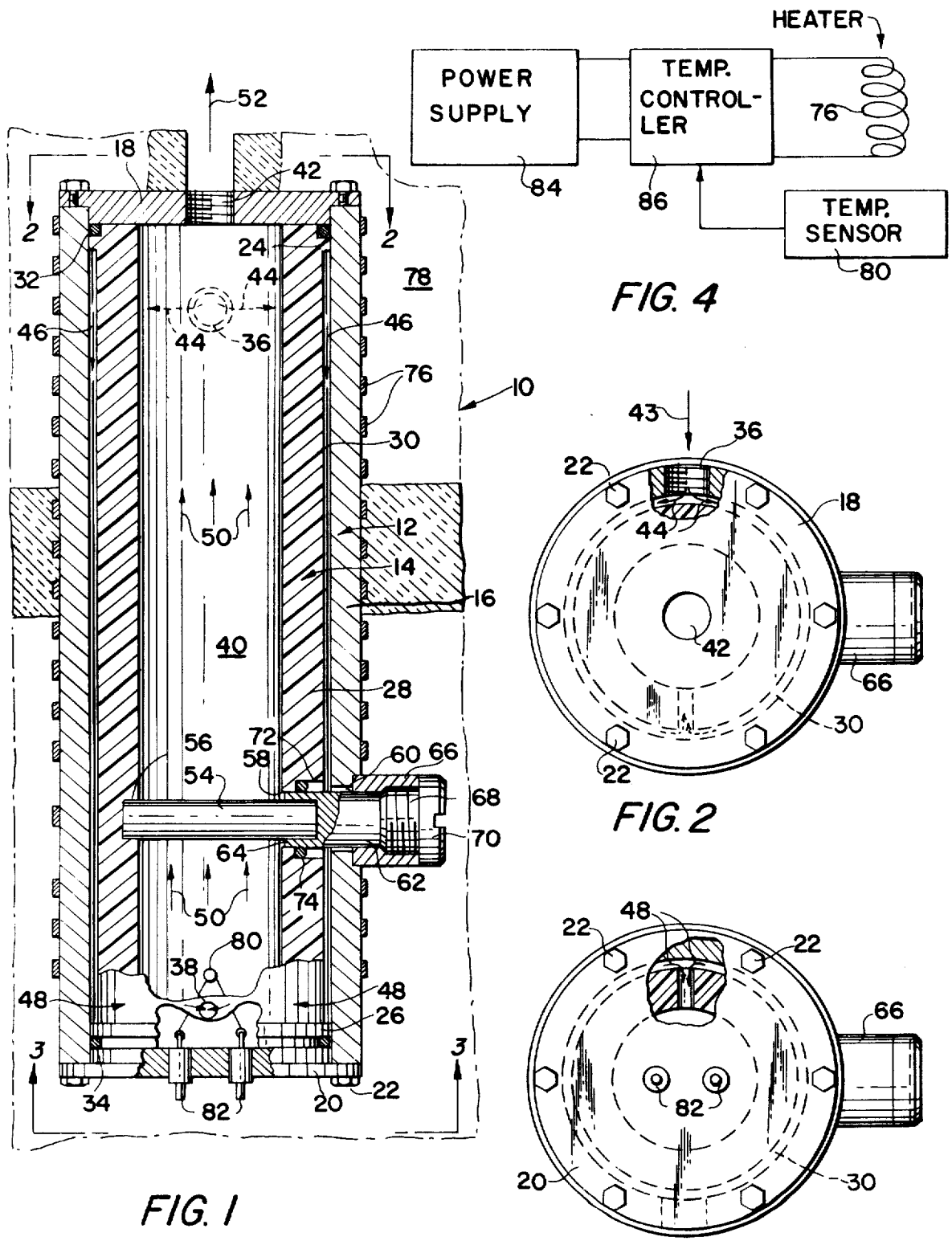

TEMPERATURE-CONTROLLED APPARATUS FOR FLUID PERMEATION OR THE LIKE

This is a divisional application of Ser. No. 320,624, filed Jan. 2, 1973 and now U.S. Pat. No. 3,904,849.

BACKGROUND OF THE INVENTION

This invention relates to temperature-controlled apparatus and more particularly to temperature-controlled apparatus for precise control of the permeation of a fluid into a carrier fluid.

It has previously been proposed to provide controlled mixing of one fluid with another by the utilization of diverse types of dilution or proportioning techniques, such as permeation or diffusion. See, for example, U.S. Pat. Nos. 3,521,865; 3,533,272; 3,618,811; 3,209,579; 3,669,637; 2,843,138; 3,516,278; British Pat. No. 811,401; and *Review of Scientific Instruments*, March, 1955, Vol 26, No. 3, pp. 305–306. For example, by one method used in calibrating a sulphur dioxide analyzer, a permeation tube containing liquified sulphur dioxide is placed in a heater chamber or conduit through which air, serving as a carrier or dilution gas, is passed. The sulphur dioxide sample diffuses through the permeation tube wall into the air stream at a known rate, dependent upon temperature. The sulphur dioxide concentration of the gas mixture is thus precisely controlled. It is used to calibrate the analyzer accordingly.

Prior attempts to provide precisely controlled mixing of fluids or dilution of one fluid by another through permeation or diffusion techniques have left much to be desired, however, because of the complexity and expense of the apparatus required, the difficulty in obtaining reproducible results, the limited range of dilution control, and/or the inability to accommodate variations in fluid temperature and flow rate. It has been known that the amount of permeation or diffusion of a fluid through a permeable wall is a function of temperature, but prior attempts to provide precise temperature control of the permeation process have left much to be desired, despite an extensive body of prior art in the heater, heat exchanger, and temperature controller field, including, for example, U.S. Pat. Nos. 2,706,620; 2,446,367; 1,480,922; 3,368,546; 1,906,450; 1,389,166; 2,730,083; 1,519,395; 1,772,557, and 1,624,843.

BRIEF SUMMARY OF THE INVENTION

It is accordingly a principal object of the present invention to provide improved temperature controlled apparatus, and particularly improved temperature controlled apparatus for controlling the permeation or diffusion of one fluid into another, when overcomes the deficiencies of the prior art.

A further object of the invention is to provide apparatus of the foregoing type which is simple, inexpensive, easy to manufacture, easy to use, and which is compact.

Another object of the invention is to provide apparatus of the foregoing type in which the temperature of a carrier gas and a permeation tube immersed therein are precisely controlled, and hence in which the rate of diffusion of a sample into the carrier gas is precisely controlled.

Yet another object of the invention is to provide apparatus of the foregoing type which readily accommodates variations of the inlet temperature of the carrier gas, which is relatively independent of ambient conditions, and which is less sensitive to the rate of flow of the carrier gas.

Briefly stated, in accordance with a preferred embodiment of the invention a temperature-regulated enclosure is provided, essentially an isothermal enclosure, in which a permeation tube or the like is located, the permeation tube containing a supply of a fluid which is to be diffused into a carrier fluid. The enclosure provides a thin large-surface-area passage through which the carrier fluid passes and by which the carrier fluid is heated to a precisely controlled temperature. More specifically, the enclosure is constituted by a cylindrical housing having a cylindrical core therein, with the side wall of the core spaced from the side wall of the housing to provide a cylindrical passage of thin annular cross-section. The carrier fluid, such as air, is admitted to one end of this passage, and at the other end of the passage a port through the hollow core is provided for admission of the carrier fluid to the hollow interior of the core, in which the permeation tube is located. The carrier fluid passes along the length of the hollow core interior and then through an exit port from the housing. The outer surface of the housing is provided with a heater winding, the power output of which is controlled in response to a temperature sensor in the core to provide heating power for precise temperature regulation of the carrier fluid as it passes into the hollow interior of the core or longitudinally of the core. The entire housing is insulated from the ambient condition by external insulation. The permeation tube may extend transversely of the core, and access to the tube may be provided at one side of the housing or at an end thereof.

BRIEF DESCRIPTION OF THE DRAWINGS

The invention will be further described in conjunction with the accompanying drawings, which illustrate preferred and exemplary embodiments, and wherein:

FIG. 1 is a longitudinal sectional view, partially broken away, of a first embodiment of the invention;

FIG. 2 is an end view, partially broken away, as seen in the direction of arrows 2—2 of FIG. 1;

FIG. 3 is an end view, partially broken away, as seen in the direction of the arrows 3—3 of FIG. 1;

FIG. 4 is a block diagram of a circuit for regulating the temperature;

DETAILED DESCRIPTION OF THE INVENTION

Figure 5:
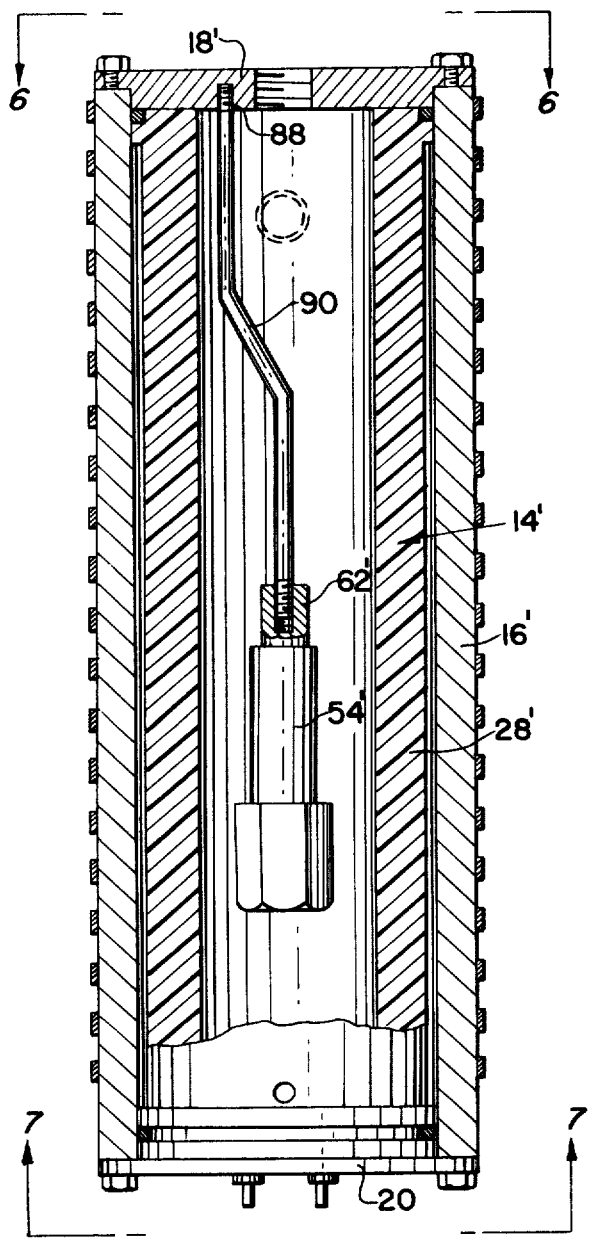
FIG. 5 is a longitudinal sectional view, partially broken away, of a modification of the invention.

Referring to the drawings, and initially to FIG. 1 thereof, the present invention comprises a temperature regulated enclosure 10 including a tubular housing 12 and a tubular core 14 contained within the housing. The housing is preferably a circular cylinder, which may be formed of aluminum, for example, having a side wall 16 and end closures 18 and 20, which may be secured to the housing as by screws 22 (see FIGS. 2 and 3). The core 14 is alos preferably a circular with a hollow interior. The core may be formed completely of Teflon, for example. The inner surfaces of the housing which as seen hereinafter are contacted by gas flowing in the enclosure, are preferably Teflon coated.

The length of the core is approximately the same as the interior length of the housing, and the core is provided with circumferential flanges 24 and 26 adjacent to the opposite ends thereof for spacing the outer surface of the side wall 28 of the core from the inner surface of the side wall 16 of the housing to provide a cylindrical passage 30 therebetween having thin annular cross-section. O-rings 32 and 34 surround the core beyond the flanges 24 and 26, respectively, to provide a seal between the side wall of the core and the side wall of the housing at opposite ends of the passage 30.

A port 36 extends through the side wall 16 of the housing adjacent to one end thereof (see FIGS. 1 and 2) to provide access to the passage 30 for the admission of fluid to one end thereof. The port may be internally threaded as shown to permit the coupling of a tube (not shown) thereto. The side wall 28 of the core is provided with a port 38 therethrough adjacent to the end of the housing opposite the end at which port 36 is provided, in order to provide communication between one end of the passage 30 and the hollow interior 40 of the core. A port 42 is provided through the end wall 18 of the housing (adjacent to port 36) by which fluid may leave the hollow interior 40. Port 42 may be internally threaded as shown in order to permit connection with a tube (not shown).

Port 42 may be connected to a vacuum pump (not shown) for moving a carrier fluid, such as clean air, through the temperature-regulated enclosure (or port 36 may be connected to a source of positive pressure). The carrier fluid enters port 36 and one end of passage 30, as indicated by arrow 43. The fluid moves circumferentially around the core 14 and longitudinally along the passage 30, as indicated by arrows 44 and 46. At the opposite end of the passage the carrier fluid moves circumferentially about the core, as indicated by arrows 48, and enters the port 38. Then the fluid moves longitudinally through a further flow passage provided by the hollow interior 40 of the core, as indicated by arrows 50, and leaves the enclosure by the port 42, as indicate by arrow 52.

Within the enclosure is a permeable wall, one side of which is exposed to the carrier fluid in the hollow interior 40 of the core, and the other side of which is exposed to a supply of a fluid to be diffused into the carrier fluid. In the form shown the wall is constituted by the side wall of a permeation tube 54 of a type well known in the art. The permeation tube may be a Teflon tube, for example, containing a supply of liquified sulphur dioxide which diffuses through the permeation tube wall into the stream of carrier gas in the hollow core. A recess 56 is provided internally of the side wall 28 of the core, and aligned openings 58 and 60 are provided in the side wall 28 of the core and the side wall 16 of the housing, through which the permeation tube 54 may be inserted into the core. A holder 62 has a cup 64 into which one end of the permeation tube is received, the other end being received in the recess 56. A boss 66 extends outwardly from the side wall 16 of the housing and is internally threaded to mate with external threads 68 on the holder 62, the outer end of which may be provided with a screw head 70. The opening 58 in the side wall 28 of the core may be undercut at 72 to receive an O-ring 74 to prevent fluid communication between passage 30 and the hollow interior 40 of the core through opening 58.

The rate at which the fluid in the permeation tube diffuses into the carrier gas is a function of the permeation tube temperature and indirectly a function of the temperature within the enclosure 10. In order that the mixture of the fluids may be precisely controlled, it is necessary that the temperature of the carrier gas and permeation tube be regulated. For this purpose a heater coil 76, such as insulated electrical heater tape, is wound helically about the exterior surface of the said wall 16 of the housing, and the entire housing is enclosed in thermal insulation 78, which may be in the form of foam rings stacked upon the housing, for example. The temperature within the hollow core may be sensed by a thermister 80 connected to terminals 82 on end wall 20 of the housing.

As shown in FIG. 4, the heater 76 is energized from a power supply 84 through a temperature controller 86, which is responsive to the temperature sensor 80. The temperature controller may be a conventional solid state or other type of device which precisely regulates the electric power supplied to the heater 76 in response to the temperature sensor 80 and which may be adjusted to select a desired temperature. Such temperature controllers are well known in the art.

It will be noted that the carrier fluid moves along the passage 30 as a thin sheet of large surface area in intimate contact wih the side wall 16 of the housing upon which the heater winding 76 or heat exchanger is mounted. A long large-surface-area flow path is provided for the carrier fluid in order to ensure that the carrier is heated and precisely controlled to a predetermined temperature. The enclosure 10 is isolated from ambient conditions by the insulation 78 to further ensure temperature control and conserve power. In accordance with the invention it is possible to ensure temperature regulation of the carrier fluid to within plus or minus. 0.01° C, for example, over a large range of carrier fluid input temperatures and flow rates. Equilibrium conditions are quickly reached and temperature variations in the admitted carrier fluid are quickly compensated by the large thermal mass, the walls of the enclosure being very thick compared to the thickness of passage 30. Compactness and efficiency are promoted by the reverse carrier gas flow through the enclosure, the permeable wall being beyond the cylindrical passage 30 of thin annular cross-section but within the confines of the passage. No preheater is required and the provision of the heater 76 only on the exterior of housing 12 (not on the core or the inside of the housing) greatly simplifies the construction.

Figure 6:
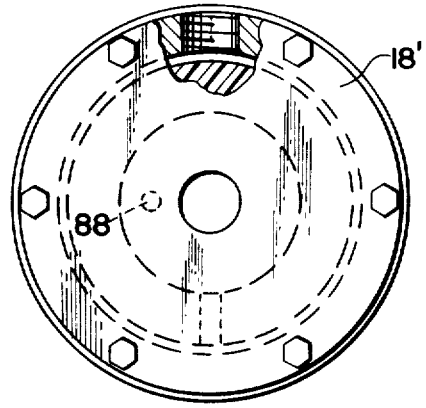
FIG. 6 is an end view, partially broken away, as seen in the direction of arrows 6—6 of FIG. 5.
Figure 7:
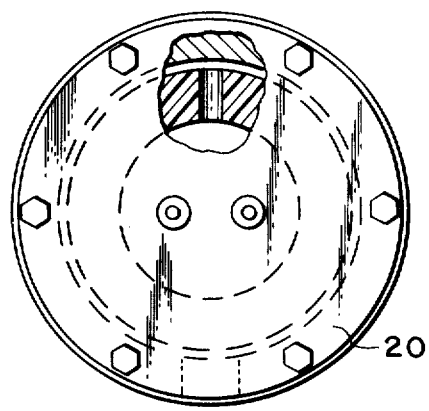
FIG. 7 is an end view, partially broken away, as seen in the direction of arrows 7—7 of FIG. 5.

A modification of the invention is illustrated in FIGS. 5-7. This embodiment of the invention is essentially the same as that previously illustrated (the external insulation not being shown in the drawing) except that a permeation tube 54' is supported longitudinally within the hollow interior of the core 14' instead of transversely. The side wall 16' of the housing and the side wall 28' of the core are devoid of the holes and recess provided in FIG. 1 for insertion and support of the permeation tube. Instead, the end wall 18' of the housing has a threaded recess 88 into which a bent rod 90 is threaded, the opposite end of the rod being threaded into a permeation tube holder 62'.

In one practical configuration of the invention the housing 12 is 7.19 inches long with an outer diameter of 2.50 inches and an inner diameter of 2.00 inches. The core 14 is 6.87 inches long with an outer diameter (neglecting the flanges) of 1.98 inches and an inner diameter of 1.25 inches, the flanges having an outer diameter matched to the inner diameter of the housing.

While preferred embodiments of the invention have been shown and described, it will be apparent to those skilled in the art that changes can be made in these embodiments without departing from the principles and spirit of the invention, the scope of which is defined in the appended claims. For example, other types of permeable walls may be employed for the diffusion of fluids diffusable through such walls.

The invention claimed is:

1. Permeation apparatus comprising a cylindrical housing with a metal cylindrical side wall, a hollow cylindrical core with a cylindrical side wall coaxially within said housing, the outer surface of the cylindrical side wall of said core and the inner surface of the cylindrical side wall of said housing delimiting therebetween a thin flow passage for conducting carrier gas between opposite ends of said core over the periphery of said core, the thickness of said flow passage being small compared with the thickness of said housing side wall and said passage having a high ratio of length to thickness, means for admitting carrier gas to one end of said flow passage, means coupling the other end of said flow passage to one end of the interior of said core, closures for said housing at opposite ends thereof, said flow passage being isolated from the interior of the core at said one end of said passage, whereby the carrier gas is constrained to flow along the length of said passage and then to enter the interior of the core at said one end thereof, means for providing an outlet from said core at the opposite end thereof, means for supporting in the interior of said core a permeation fluid container having a wall permeable to fluid in the container, heater means comprising an electrical heater mounted exteriorly of the housing side wall for supplying heat to the exterior of said housing, means including a temperature sensor sensing the temperature of the carrier gas which enters the interior of the core for controlling said heater means to control the temperature in said housing, and insulation means for isolating the exterior of said housing from the ambient.

2. Apparatus in accordance with claim 1, wherein the outer surface of said core side wall and the inner surface of said housing side wall are uniformly separated substantially from one end of the core to the other end to provide said passage with a thin annular cross-section whereby carrier fluid can flow through said passage as a thin cylindrical sheet.

3. Apparatus in accordance with claim 1, wherein the thickness of said passage is of the order of 0.01 inch.

4. Apparatus in accordance with claim 1, wherein said means for supporting said permeation fluid container comprises means for inserting said container into said core transversely through the side walls of said housing and said core.

5. Apparatus in accordance with claim 1, wherein said means for supporting said permeation fluid container comprises means for inserting said container into said core longitudinally of said core.

6. Apparatus in accordance with claim 1, wherein said core has external circumferential flanges at opposite ends thereof engaging the side wall of said housing and spacing the side wall of said core from the side wall of said housing.

7. Apparatus in accordance with claim 1, wherein said admitting means comprises a port through a side of said housing side wall, wherein said coupling means comprises a port through the opposite side of the core side wall, wherein said closures engage opposite ends of said cored, respectively and wherein said outlet comprises a port through one of said closures coupled to the interior of said core.

* * * * *